(12) United States Patent
Giladi

(10) Patent No.: US 10,188,134 B2
(45) Date of Patent: *Jan. 29, 2019

(54) AUTHENTICATED ENCRYPTION SUPPORT IN DASH BASED SEGMENTED STREAMING MEDIA DISTRIBUTION

(71) Applicant: Futurewei Technologies, Inc., Plano, TX (US)

(72) Inventor: Alexander Giladi, Princeton, NJ (US)

(73) Assignee: FUTUREWEI TECHNOLOGIES, INC., Plano, TX (US)

( * ) Notice: Subject to any disclaimer, the term of this patent is extended or adjusted under 35 U.S.C. 154(b) by 317 days.

This patent is subject to a terminal disclaimer.

(21) Appl. No.: 14/921,902

(22) Filed: Oct. 23, 2015

(65) Prior Publication Data

US 2016/0105403 A1 Apr. 14, 2016

Related U.S. Application Data

(63) Continuation of application No. 14/049,609, filed on Oct. 9, 2013, now Pat. No. 9,203,811.

(Continued)

(51) Int. Cl.
*H04L 29/06* (2006.01)
*H04L 9/08* (2006.01)
(Continued)

(52) U.S. Cl.
CPC ............ *A23L 33/135* (2016.08); *A01N 25/22* (2013.01); *A23K 10/18* (2016.05); *A23K 20/147* (2016.05);
(Continued)

(58) Field of Classification Search
CPC . H04L 63/0428; H04L 9/0816; H04L 9/0637; H04L 9/0668; H04L 2209/24;
(Continued)

(56) References Cited

U.S. PATENT DOCUMENTS

2008/0165953 A1* 7/2008 Patel ................... G06F 21/606
380/28
2009/0013016 A1* 1/2009 Noll ................... G06F 21/6209
(Continued)

OTHER PUBLICATIONS

"Information Technology—Dynamic Adaptive Streaming over HTTP (DASH)—Part 1: Media Presentation Description and Segment Formats," ISO/IEC JTC 1/SC 29, ISO/IEC 23009-1:2012(E), ISO/IEC JTC 1/SC 29/WG 11, Jan. 5, 2012, 133 pages.

(Continued)

*Primary Examiner* — Ashokkumar B Patel
*Assistant Examiner* — Quazi Farooqui
(74) *Attorney, Agent, or Firm* — Futurewei Technologies, Inc.

(57) ABSTRACT

A server apparatus supporting authenticated encryption in a network, comprising a receiver configured to receive an unencrypted segment, a processor configured to selecting an encryption key, an initialization vector, and an additional authentication data (AAD), encrypt the segment, configuring the segment for transfer in a Dynamic Adaptive Streaming over Hypertext Transfer Protocol (HTTP) (DASH) media, assign a segment number to the encrypted segment, append an authentication tag to the encrypted segment, store the encrypted segment with the appended authentication tag, and update a Media Presentation Description (MPD) associated with the encrypted segment with the appended authentication tag, wherein the MPD comprises an @aadBase attribute with an AAD base value, wherein the AAD value is the sum of the segment number and the @aadBase attribute value, and a transmitter configured to transmit the encrypted segment with the appended authentication tag to a destination.

18 Claims, 4 Drawing Sheets

Related U.S. Application Data

(60) Provisional application No. 61/711,532, filed on Oct. 9, 2012.

(51) Int. Cl.

| | | |
|---|---|---|
| *A23L 33/135* | (2016.01) | |
| *A61K 47/42* | (2017.01) | |
| *A61K 47/36* | (2006.01) | |
| *A61K 47/26* | (2006.01) | |
| *A01N 25/22* | (2006.01) | |
| *A61K 9/19* | (2006.01) | |
| *A23L 33/105* | (2016.01) | |
| *A23L 33/14* | (2016.01) | |
| *A23L 33/18* | (2016.01) | |
| *A23L 33/19* | (2016.01) | |
| *A23K 20/147* | (2016.01) | |
| *A23K 20/163* | (2016.01) | |
| *A23K 20/174* | (2016.01) | |
| *A23K 50/40* | (2016.01) | |
| *A23K 10/18* | (2016.01) | |
| *A23L 33/125* | (2016.01) | |
| *A23L 33/15* | (2016.01) | |
| *A61K 47/40* | (2006.01) | |

(52) U.S. Cl.
CPC .......... *A23K 20/163* (2016.05); *A23K 20/174* (2016.05); *A23K 50/40* (2016.05); *A23L 33/105* (2016.08); *A23L 33/125* (2016.08); *A23L 33/14* (2016.08); *A23L 33/15* (2016.08); *A23L 33/18* (2016.08); *A23L 33/19* (2016.08); *A61K 9/19* (2013.01); *A61K 47/26* (2013.01); *A61K 47/36* (2013.01); *A61K 47/40* (2013.01); *A61K 47/42* (2013.01); *A23V 2002/00* (2013.01)

(58) Field of Classification Search
CPC ....... H04L 2209/60; H04L 29/06; H04L 9/08; H04N 21/23476; H04N 21/25816; G06F 2221/2107
USPC ...................... 713/168, 161, 169, 170; 726/2
See application file for complete search history.

(56) References Cited

U.S. PATENT DOCUMENTS

| | | |
|---|---|---|
| 2013/0276035 A1 | 10/2013 | Walker et al. |
| 2014/0019635 A1* | 1/2014 | Reznik ................ H04L 65/607 709/231 |
| 2014/0317234 A1 | 10/2014 | Mueller et al. |

OTHER PUBLICATIONS

"Information Technology—Dynamic Adaptive Streaming over HTTP (DASH)—Part 1: Media Presentation Description and Segments Formats," International Standard ISO/IEC 23009-1, First Edition, Apr. 1, 2012, 134 pages.
Krawczyk et al., "HMAC: Keyed-Hashing for Message Authentication," RFC 2140, Feb. 1997, 12 pages.
Fielding et al., "Hypertext Transfer Protocol—HTIP/1.1," RFC 2616, Jun. 1999, 177 pages.
Berners-Lee et al., "Uniform Resource Identifier (URI): Generic Syntax," RFC 3986, Jan. 2005, 62 pages.
Dierks et al., "The Transport Layer Security (TLS) Protocol Version 1.2," RFC 5246, Aug. 2008, 105 pages.
Housley et al., "Cryptographic Message Syntax (CMS)," RFC 5652, Sep. 2009, 57 pages.
"Information Technology—MPEG systems technologies—Part 7: Common encryption in ISO base media file format files," International Standard, ISO/IEC, 23001-7, Feb. 1, 2012, 18 pages.
"Information Technology—Dynamic Adaptive Streaming over HTTP (DASH)—Part 4: Segment Encryption and Authentication," ISO/IEC JTC 1/SC 29, ISO/IEC FCD 23009-4, XP030019365, Aug. 4, 2012, 29 pages.
"Information Technology—Dynamic Adaptive Streaming over HTTP (DASH)—Part 1: Media Presentation Description and Segment Formats," ISO/IEC JTC 1/SC 29, ISO/IEC DIS 23009-1, XP002687350, Aug. 30, 2011, 131 pages.
Giladi, A., "Authenticated Encryption Support in 23009-4," International Organisation for Standardisation, ISO/IEC JTC1/SC29/5 WG11, Coding of Moving Pictures and Audio, ISO/IEC JTC1/SC/WG11 MPEG2012/M26891, Shanghai, China, XP030055224 Oct. 12, 2012, 5 pages.
McGrew, D.A. et al., "The Galois/Counter Mode of Operation (GCM)," Internet Citation retrieved from the internet on Jan. 1, 2004, XP002456593, 43 pages.
Viega, J. et al., "The Use of Galois/Counter Mode (GCM) in IPsec Encapsulating Security Payload (ESP)," RFC4106, XP015041895, Jun. 2005, 11 pages.

* cited by examiner

AUTHENTICATED ENCRYPTION SUPPORT IN DASH BASED SEGMENTED STREAMING MEDIA DISTRIBUTION

CROSS-REFERENCE TO RELATED APPLICATIONS

The present application is a continuation of U.S. patent application Ser. No. 14/049,609 filed on Oct. 9, 2013 by Alexander Giladi and titled "Authenticated Encryption Support in ISO/IEC 23009-4", which claims priority to U.S. Provisional Patent Application No. 61/711,532 filed Oct. 9, 2012 by Alexander Giladi and titled "Authenticated Encryption Support in DASH Part 4," both of which are incorporated by reference herein in their entireties.

STATEMENT REGARDING FEDERALLY SPONSORED RESEARCH OR DEVELOPMENT

Not applicable.

REFERENCE TO A MICROFICHE APPENDIX

Not applicable.

BACKGROUND

A media content provider or distributor may transmit media contents to streaming clients, which may take the form of various user end devices, such as televisions, notebook computers, and mobile handsets. Media content may comprise a Media Presentation Description (MPD) and a plurality of segments, which may be delivered over a network. The MPD may be an extensible markup language (XML) file or document describing the media content, such as its various representations, Uniform Resource Locator (URL) addresses, and other characteristics. For example, the media content may comprise several media components (e.g., audio, video, and text), each of which may have different characteristics that are specified in the MPD. Each media component comprises a plurality of media segments containing the parts of actual media content, and the segments may be stored collectively in a single file or individually in multiple files. Each segment may contain a predefined byte size (e.g., 1,000 bytes) or an interval of playback time (e.g., 2 or 5 seconds) of the media content.

Media content may be delivered from a streaming server to a streaming client adaptively based on a variety of factors, such as network conditions, device capability, and user choice. Upon reception of the media, the streaming client may parse the media to extract information from within. Adaptive streaming technologies may include various technologies or standards implemented or being developed, such as Dynamic Adaptive Streaming over Hypertext Transfer Protocol (HTTP) (DASH), HTTP Live Streaming (HLS), Adaptive Transport Streaming (ATS), or Internet Information Services (IIS) Smooth Streaming. DASH defines a manifest format, MPD, and segment formats for International Organization for Standardization (ISO) Base Media File Format (ISO-BMFF) and Moving Picture Experts Group (MPEG) 2 (MPEG-2) Transport Streams.

DASH is a standard developed to provide media content and is partially described in ISO/International Electrotechnical Commission (IEC) 23009-1, First Edition, 2012 ("23009-1"), which is incorporated herein by reference as if reproduced in its entirety. For content encryption, MPEG has developed certain frameworks, e.g., the frameworks recounted in ISO/IEC documents numbered 23001-7, titled "MPEG systems technologies—Part 7: Common encryption in ISO base media file format files," and 23009-4, titled "Dynamic Adaptive Streaming over HTTP (DASH)—Part 4: Segment Encryption and Authentication" (ISO/IEC 23009-4) (referred to herein as "Part 4"), both of which are incorporated herein by reference as if reproduced in their entirety.

DASH comprises at least two devices, one or more HTTP servers that provide the content and the DASH client that downloads the content and is associated with the viewer, or user. DASH leaves control with the client, which can request content using the HTTP protocol. DASH is dynamic and adaptive; the client may choose from among multiple forms of content, or data, based on a variety of factors such as network conditions, device capability, and user choice. For example, the HTTP server may inform the client of different download bit rates, the client may choose one of the bit rates, and the client may begin downloading segments of data at the chosen bit rate. If for some reason network conditions deteriorate, then the client may change to a lower bit rate and begin downloading segments of data at the new bit rate. DASH's adaptability therefore ensures that the client consumes less than the available bandwidth.

SUMMARY

In one embodiment, the disclosure includes a server apparatus supporting authenticated encryption in a network, comprising a receiver configured to receive an unencrypted segment, a processor configured to select an encryption key, an initialization vector, and an additional authentication data (AAD), encrypt the segment, configure the segment for transfer in a DASH media, assign a segment number to the encrypted segment, append an authentication tag to the encrypted segment, store the encrypted segment with the appended authentication tag, and update a MPD associated with the encrypted segment with the appended authentication tag, wherein the MPD comprises an @aadBase attribute with an AAD base value, wherein the AAD value is the sum of the segment number and the @aadBase attribute value, and a transmitter configured to transmit the encrypted segment with the appended authentication tag to a destination.

In another embodiment, the disclosure includes a computer program product comprising computer executable instructions stored on a non-transitory medium that when executed by a processor cause the processor to receive an unencrypted segment, select an encryption key, an initialization vector, and an AAD, encrypt the segment, wherein the segment is encrypted using an Advanced Encryption Standard (AES) cipher in Galois/Counter Mode (GCM) mode with an initialization vector with a length given by an @authTagLength attribute of a SegmentEncryption element and an authentication tag with a length given by an @authTagLength attribute of the SegmentEncryption element, append the authentication tag to the encrypted segment, configure the encrypted segment with the appended authentication tag for transfer in a DASH media, assign a segment number to the encrypted segment, store the encrypted segment with the appended authentication tag, update an MPD associated with the encrypted segment with the appended authentication tag, wherein the MPD comprises an @aadBase attribute with an AAD base value, wherein the AAD value is the sum of the segment number and the @aadBase attribute value, and transmit the encrypted segment with the appended authentication tag to a destination.

In yet another embodiment, the disclosure includes a method of supporting authenticated encryption at a client node in a network, the method comprising receiving a DASH media comprising an encrypted data segment, wherein the media comprises a @SegmentEncryption@ivEncryptionFlag attribute, a SegmentEncryption@ivLength attribute, a segment number, and information sufficient to permit the client node to query a server for a decryption key, obtain a decryption key from the server, derive an initialization vector and an AAD, authenticate an origin of the encrypted data segment, and decrypt the encrypted data segment, wherein the initialization vector is the segment number when the SegmentEncryption@ivEncryptionFlag value is 'false' and the media comprises a CryptoPeriod element, wherein the initialization vector is a sum of the segment number and an @ivBase attribute when the SegmentEncryption@ivEncryptionFlag value is 'false' and the media comprises a CryptoTimeline element, wherein the initialization vector is an Electronic Codebook (ECB)-encrypted value of a transmitted initialization vector when the SegmentEncryption@ivEncryptionFlag value is 'true' and the media does not comprise a CryptoTimeline element or a CryptoPeriod element, wherein the initialization vector is an ECB-encrypted value of the segment number when the SegmentEncryption@ivEncryptionFlag value is 'true' and the media comprises a CryptoPeriod element, wherein the initialization vector is an ECB-encrypted value of the sum of the segment number and the @ivBase when the SegmentEncryption@ivEncryptionFlag value is 'true' and the media comprises a CryptoTimeline element, and wherein the initialization vector is a first SegmentEncryption@ivLength most significant bit from ECB output when the SegmentEncryption@ivEncryptionFlag value is 'true' and the SegmentEncryption@ivLength is smaller than an output block size of the ECB output.

These and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
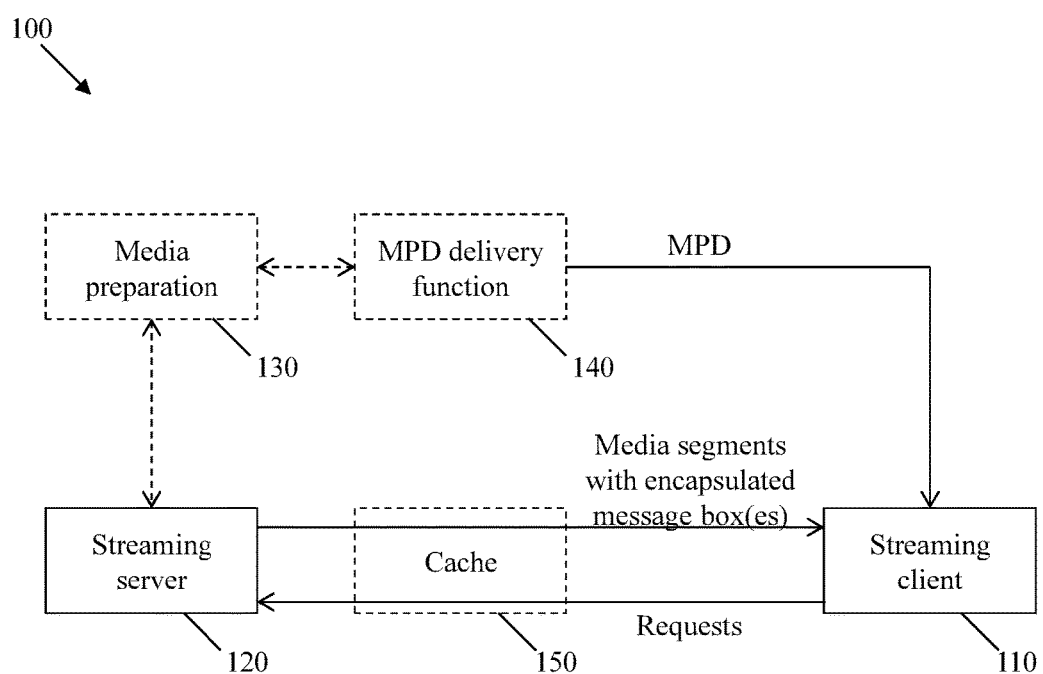
FIG. 1 is a schematic diagram of an embodiment of a DASH-enabled streaming architecture.

It should be understood at the outset that, although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

DASH is historically agnostic to digital rights management (DRM), and presently supports signaling DRM scheme and its properties within the MPD. A DRM scheme can be signaled via the ContentProtection descriptor, which may pass an opaque value within it. DASH currently does not provide a generic mechanism for identifying and/or authenticating the encrypting entity.

This disclosure includes utilizing new and existing elements and attributes in a DASH MPD data stream to support authenticated encryption, or rather a mode of operation in which the plaintext is encrypted into the ciphertext and an authentication tag is generated based on Additional Authentication Data (ADD) and the ciphertext. As used herein, the phrase DASH media may mean an MPD and one or more segments, and may comprise several iterations of the same. As used herein, a segment may mean data containing an interval of electronically playable content, e.g., video, audio, or both. Conceptually, the content protection framework provided in this disclosure may be viewed as two entities, key system and encryption system. Key system derives keys associated with a segment given the information provided in the MPD, while the encryption system decrypts media segments given the information provided in the MPD and encryption keys provided by the key system. Embodiments disclosed herein may encrypt only the media segments and not the MPD that describes them.

This disclosure further includes a framework for allowing the use of digital authenticity tags for all DASH segment types in order to verify the origin and content authenticity and, in some embodiments, DRM. As used herein, the phrase authentication tag may mean a cryptographic hash or a message authentication code on data that is designed to reveal both accidental errors and the intentional modification of the data. This framework works by calculating a digest or a message authentication code (MAC) of an unencrypted segment, and storing the value externally. The MPD interface provides URL templates to retrieve these, using HTTP Secure (HTTPS) or HTTP. The client may retrieve the authentication tag, may calculate the tag locally on the decrypted segment, and may reject the segment in case of a mismatch. If used with encryption, the mode of operation of this framework may utilize an "authenticate, then encrypt" paradigm rather than the more common "encrypt, then authenticate" paradigm. The former may provide an important feature of encryption invariance: if no encryption, or different encryption algorithm and/or parameters were used for encryption of the same media segment for serving it to different clients, the authenticity tag may stay the same as long as the content itself has not changed. Segment Authentication may be independent of any content protection scheme, and may be used on unencrypted segment as well as on encrypted segments encrypted using any DRM system.

FIG. 1 illustrates an embodiment of a DASH-enabled streaming architecture 100, which may be implemented to deliver media content from a streaming server or provider 120 to a streaming client 110. The streaming client 110 may be a program or application implemented in an operating system of a user device, or it may be a web client accessed in a web platform. The streaming client 110 may be any device configured to obtain media content via a DASH protocol and present such media content to a user, such as a mobile phone, personal computer (PC), Internet Protocol (IP) television (TV), IP TV set top box, laptop PC, internet radio device, tablet PC, media storage device, etc. The streaming client 110 may be a DASH client, and the streaming server may be an HTTP server or proxy. The streaming server 120 may be any device configured to service requests from the streaming client 110 and may optionally/alternatively comprise an HTTP server, a key server, an initialization vector (IV) server, and/or a license server, as would be understood by those of skill in the art.

The media content stored in the streaming server 120 may be generated or prepared by a streaming media preparation unit 130. The media preparation unit 130 may be located in the streaming server 120 or elsewhere (e.g., in a content provider). The streaming server 120 may be part of a content provider or may be a node in a content distribution network (CDN). For example, the streaming server 120 may be an edge node in a CDN, and may work as the last hop from a content provider to the streaming client 110. The media content may be generated by the content provider and then transmitted to a CDN node. The media content in the streaming server 120 may comprise an MPD and a plurality of segments. Note that, if desired, the MPD and the segments may be stored in different servers and sent to the streaming client 110 from different servers. In addition, a streaming server described herein merely serves as an example of a server, it should be understood that thus embodiments disclosed herein may also be implemented in any other suitable type of server.

The streaming client 110 may send a request to the streaming server 120 for media content. In response, the streaming server 120 may first use an MPD delivery function 140 to deliver an MPD to the streaming client 110. The MPD may be delivered using HTTP, email, thumb drive, broadcast, or any other transport. By parsing the MPD, the streaming client 110 may learn information regarding the media content, such as the timing of the program, the availability of media content, the media types, resolutions, minimum and maximum bandwidths, the existence of various encoded alternatives of multimedia components, the accessibility features and the required DRM, the location of each media component on the network, and other characteristic of the media content. Using this information, the streaming client 110 may select the appropriate encoded representation or alternative and start streaming the media content by fetching media segments, e.g., in one of the supported DASH media segment formats.

The streaming server 120 may use a segment delivery function to deliver a media segment to the streaming client 110. The streaming client 110 may download segments from a plurality of streaming servers, e.g., to maximize usage of network bandwidth. The streaming client 110 may render the downloaded media appropriately so as to provide streaming service to a user of the streaming client 110. Although the streaming client 110 may obtain the segments based on locations specified by URLs contained in the MPD, sometimes the segment may be stored in an HTTP cache 150 (e.g., in the streaming server 120), so that the streaming client 110 may receive them more efficiently.

The MPD may contain certain common attributes and elements, as described in ISO/IEC 23009-1, titled "Dynamic Adaptive Streaming over HTTP (DASH)—Part 1: Media presentation description and segment formats," (referred to herein as "Part 1") incorporated herein by reference. One such element is the ContentProtection element, which may specify information about content protection schemes used for the associated Representations. The MPD may also contain descriptors that provide a flexible mechanism for DASH content authors to annotate and extend the MPD, Period, AdaptationSet and Representation elements. The semantics of the attributes within an element of the type ContentProtection may be as described in Part 1 and/or Part 4, e.g., using the following syntax and semantics:

| Element or Attribute Name | Use | Description |
| --- | --- | --- |
| ContentProtection | | |
| @schemeIdUri | M | Shall be urn:mpeg:dash:sea:enc:2013 for this part of the standard. |
| sea:SegmentEncryption | 1 | Specifies the encryption system used and its global properties. |
| sea:License | 0 . . . N | Specifies the key system used and ways of getting license, if needed. |
| sea:CryptoPeriod | 0 . . . N | Specifies information needed for derivation of key and IV information for a single cryptoperiod. |
| sea:CryptoTimeline | 0 . . . N | Specifies information needed for derivation of key and IV information for several constant-length cryptoperiods. |

Legend:
For attributes: M = Mandatory, O = Optional, OD = Optional with Default Value, CM = Conditionally Mandatory.
For elements: <minOccurs> . . . <maxOccurs> (N = unbounded)
Elements are bold; attributes are non-bold and preceded with an @.

The SegmentEncryption element may describe the global properties of segment encryption as used in all cryptoperiods, and may have the semantics set forth in Part 4. The License element may describe the global properties of a key system used in all cryptoperiods, and may have the semantics set forth in Part 4. As used herein, a cryptoperiod may mean a number of continuous segments for which the same encryption key and the same initialization vector may be used. The CryptoPeriod element may define a single cryptoperiod, namely, it may provide information allowing derivation of an encryption key and an IV, as well as identifying segments which were encrypted using the former two elements, and may have the semantics set forth in Part 4. A CryptoPeriod element may correspond uniquely to a start segment, and may have the semantics set forth in Part 4. The CryptoPeriod element may have an explicitly specified duration (e.g., number of segments), or may be unbounded (e.g., continue until the end of the current Period), and may have the semantics set forth in Part 4.

Thus, only media segments may be encrypted using the encryption system identified by the SegmentEncryption@schemeIdUri attribute. Initialization, Index, and Bitstream Switching segments may not be encrypted. Any concatenation involving encrypted segments may apply after decryption. Implementation of the appropriate encryption system may be essential; hence a client that does not implement the encryption algorithm specified in SegmentEncryption@schemeIdUri should not attempt to present any encrypted media segment.

The AES-128 GCM full-segment encryption system may be identified by the Uniform Resource Name (URN) urn: mpeg:dash:sea:aes128-gcm:2013. Support for this scheme may be optional for clients implementing Part 4. In this algorithm, AES cipher may be used in GCM mode with 96-bit IVs and 128-bit authentication tags. Encryption shall be applied to complete segments. A single combination of key and IV may be used only once during the whole Period. As a consequence, a cryptoperiod in this encryption system may only consist of a single segment, and there may be no identical key/IV combinations within the Period. The authentication tag may be appended to the last byte of the segment (e.g., the encrypted segment may be @authTagLength bytes longer than the unencrypted one).

The disclosure includes embodiments that may extend the existing signaling mechanisms, e.g., by adding and/or expanding attributes for specifying AAD, specifying the IV base value for a cryptoperiod, specifying the AAD base value for a cryptoperiod, etc. Utilizing one or more disclosed embodiments may support authenticated encryption in DASH.

The disclosed embodiments may extend the signaling mechanisms above by including a CryptoPeriod element having the following semantic characteristics:

respond to a cryptoperiod (CP(M,D)). As used herein, the phrase segment number may mean a unique positive integer associated with a Media Segment within a Representation. For example, the Media Segment presented (in presentation order) after Media Segment with Segment Number N has Segment Number N+1. For cryptoperiod CP(M,D), segments S(M), S(M+1), S(M+1), . . . S(M+D−1) may be encrypted with the same key/IV combination, $KCP_{(M,D)}$, and $IV_{CP(M,D)}$. If these are not signaled explicitly, the key and IV derivation rules outlined in Part 4 may apply. A single CryptoTimeline may be used to derive CryptoTimeline@numCryptoPeriod cryptoperiods, each containing CryptoTimeline@numSegment segments. The first cryptoperiod in a CryptoTimeline may be @firstStartOffset segments after the end of the previous cryptoperiod. If this first cryptoperiod is the first during this Period, @firstStartOffset may be relative to the start of the Period. For a CryptoTimeline element, with first Segment Number M, @numCryptoPeriods=N, and @numSegments=D, for $0 \leq k \leq N$, the $k^{th}$ cryptoperiod generated using this CryptoTimeline element is CP(M+k×D, D). If the CryptoPeriod or CryptoTimeline are the last elements in this Period, and cryptoperiod duration is not explicitly stated by CryptoTimeline@numSegments or CryptoPeriod@numSegments, it may be assumed that the current cryptoperiod continues till the end of the Period. Note that in case of CryptoTimeline this implies that there may be only one cryptoperiod within such a CryptoTimeline. If neither a CryptoPeriod nor a CryptoTimeline are present, all segments may be unencrypted. Any segments

| Element or Attribute Name | Use | Description |
| --- | --- | --- |
| CryptoPeriod | | Specifies information and URIs needed for derivation of key information for a single cryptoperiod. |
| @startOffset | OD | Specifies the number of unencrypted segments after the end of the previous cryptoperiod and the first Media Segment to which the key/IV information applies. Default value is 0. |
| @IV | O | Specifies the IV. It shall not be present if @ivUriTemplate is present. |
| @aad | O | Specifies the AAD. AAD derivation rules may be specified in Part 4. |
| CryptoPeriodType | — | specifies the common attributes and elements (attributes and elements from base type CryptoPeriodType). |

Legend:
For attributes: M = Mandatory, O = Optional, OD = Optional with Default Value, CM = Conditionally Mandatory.
For elements: <minOccurs> . . . <maxOccurs> (N = unbounded)
Elements are bold; attributes are non-bold and preceded with an @.

A CryptoPeriod element may define a single cryptoperiod, namely, it may provide information allowing derivation of an encryption key and an IV, as well as identifying segments which were encrypted using the former two elements. A CryptoPeriod element may correspond uniquely to a start segment. A CryptoPeriod element may have explicitly specified duration (e.g., a number of segments), or may be unbounded (e.g., may continue till the end of the current Period). A CryptoPeriod element may correspond to a single cryptoperiod containing @numSegments segments with and starting @startOffset segments from the end of the previous cryptoperiod. If the cryptoperiod is the first during the current Period, the value of @startOffset may be relative to the start of the Period. A CryptoPeriod element with @numSegments=D and first Segment Number M may correspond to a cryptoperiod using the rules in this subclause shall be unencrypted.

The CryptoTimeline element may be used for derivation of multiple cryptoperiods having a constant number of segments. While a single CryptoPeriod may correspond to a single cryptoperiod, a single CryptoTimeline element may correspond to multiple cryptoperiods. Use of the CryptoTimeline may be encouraged when a highly regular pattern of cryptoperiods is used, e.g. when a key/IV pair is changed every cryptoperiod. Each cryptoperiod generated from a CryptoTimeline may contain the same number of segments. The CryptoTimeline element may have the following semantic characteristics:

| Element or Attribute Name | Use | Description |
| --- | --- | --- |
| CryptoTimeline | | Specifies a sequence of cryptoperiods, each containing same amount of segments<br>Note: the time duration of cryptoperiods does not have to be constant - the constant is only number of segments. |
| @numCryptoPeriods | O | Specifies number of constant-duration cryptoperiods within this timeline. If absent, the last cryptoperiod ends with the end of the Period this ContentProtection descriptor belongs to. Note that this implies that the amount of segments in the last cryptoperiod in this case can be smaller than specified in the @numSegments attribute. |
| @firstStartOffset | OD | Specifies the number of unencrypted segments between the end of the last cryptoperiod and the first segment of the first cryptoperiod in this CryptoTimeline. Default value is 0. |
| @ivBase | OD | Specifies the IV base value for this cryptoperiod. When @ivBase is present, IV is a sum of @ivBase and Segment number. If absent, the default value is 0.<br>Shall not be present if @ivUriTemplate is present. |
| @aadBase | OD | Specifies the AAD base value for this cryptoperiod. AAD is the sum of @aadBase and the Segment Number. If absent, the default value is 0. |
| CryptoPeriodType | — | specifies the common attributes and elements (attributes and elements from base type CryptoPeriodTypeP). |

Legend:
For attributes: M = Mandatory, O = Optional, OD = Optional with Default Value, CM = Conditionally Mandatory.
For elements: <minOccurs> . . . <maxOccurs> (N = unbounded)
Elements are bold; attributes are non-bold and preceded with an @.

Media segments may be encrypted using the encryption system identified by the SegmentEncryption@schemeIdUri attribute. Initialization, Index, and Bitstream Switching segments shall not be encrypted. Any concatenation involving encrypted segments shall apply after decryption. Implementation of the appropriate encryption system is essential; hence a client that does not implement the algorithm specified in SegmentEncryption@schemeIdUri should not attempt to present any encrypted media segment.

Additionally, if the SegmentEncryption@ivEncryptionFlag value is 'false' and CryptoTimeline element is used, a sum of Segment Number (SN) and @ivBase may be used as the IV value for the CryptoPeriod ($IV_{CP}$), i.e. $IV_{CP(M,D)}$=SN+ivBase. The default value of @ivBase may be set to 0, and hence if @ivBase is absent the result may be $IV_{CP(M,D)}$=SN. If SegmentEncryption@ivEncryptionFlag value is 'true', ECB-encrypted IV's will be used. This method is described in Appendix C of National Institute of Standards and Technology (NIST) 800-38A, titled "Recommendation for Block Cipher Modes of Operation," incorporated herein as though reproduced in its entirety. If SegmentEncryption@ivEncryptionFlag value is 'true', and CryptoPeriod element is used, the IV shall be an ECB-encrypted value of Segment Number. For example, when AES-128 encryption is used (in any mode), the IV may be described by $IV_{CP(M,D)}$=AES(SN, $K_{CP(M,D)}$). If SegmentEncryption@ivEncryptionFlag value is 'true', and CryptoTimeline element is used, the IV is the ECB-encrypted sum of Segment Number and @ivBase. For example, when AES-128 encryption is used (in any mode), the IV may be described by $IV_{CP(M,D)}$=AES(SN+ivBase, $K_{CP(M,D)}$). If SegmentEncryption@ivEncryptionFlag value is 'true', and SegmentEncryption@ivLength is smaller than the output block size of the ECB output (e.g., when 96-bit IVs are used), then the first SegmentEncryption@ivLength most-significant bits from ECB output may be used as an IV.

Further, for the CryptoPeriod element, the AAD may be given by the value of CryptoPeriod@aad. For a CryptoTimeline element, Segment Number and @aadBase may be used for AAD derivation, i.e., $AAD_{CP(M,D)}$=SN+aadBase.

Figure 2:
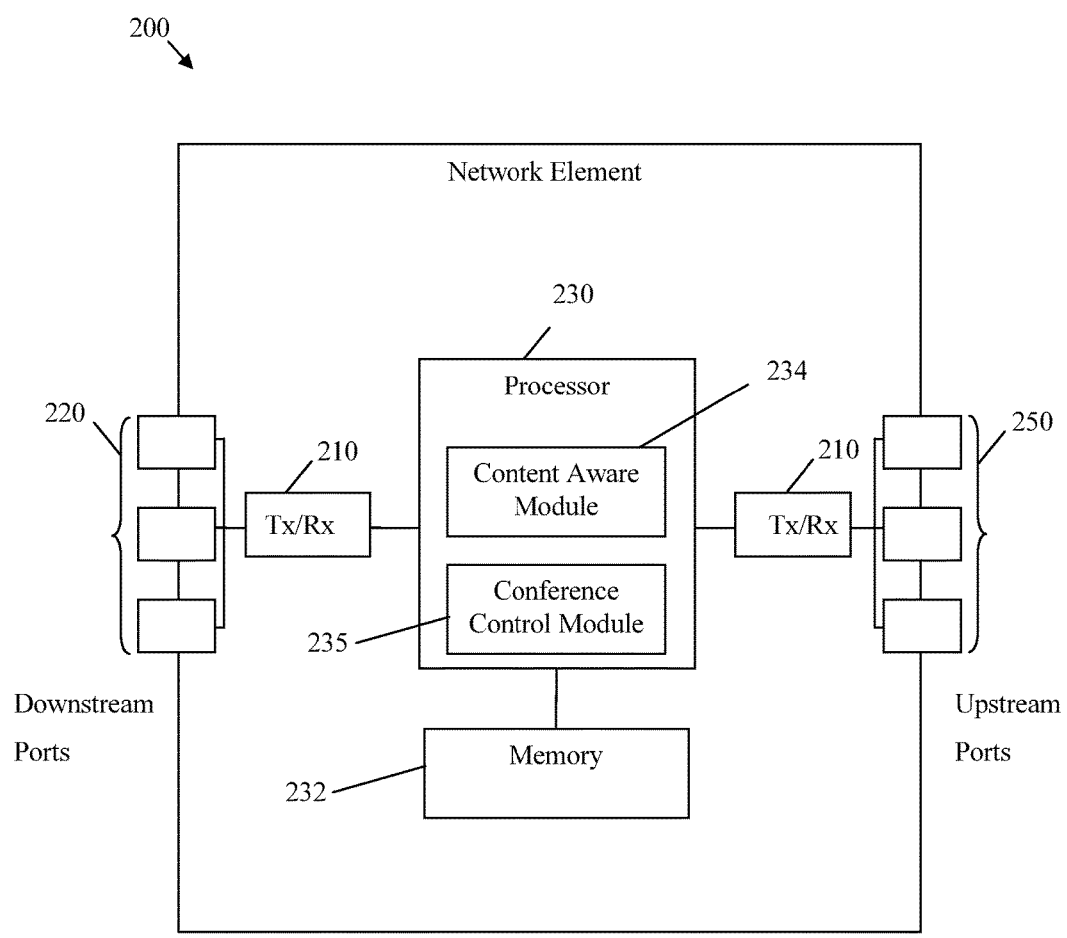
FIG. 2 is a schematic diagram of an embodiment of a network node.

FIG. 2 is a schematic diagram of an embodiment of a network node 200, which may be a streaming server 120, a streaming media preparation unit 130, or a streaming client 110. In some embodiments node 200 may also act as other node(s) in the network. Person of ordinary skill in the art will be aware that the participating client 110 may be similarly configured. One skilled in the art will recognize that the term node encompasses a broad range of devices of which node 200 is merely an example. Node 200 is included for purposes of clarity of discussion, but is in no way meant to limit the application of the present disclosure to a particular node embodiment or class of node embodiments. At least some of the features/methods described in the disclosure may be implemented in a network apparatus or component such as a node 200. For instance, the features/methods in the disclosure may be implemented using hardware, firmware, and/or software installed to run on hardware. The node 200 may be any device that transports frames through a network, e.g., a switch, router, bridge, server, a client, etc. As shown in FIG. 2, the node 200 may comprise transceivers (Tx/Rxs) 210, which may be transmitters, receivers, or combinations thereof. A Tx/Rx 210 may be coupled to plurality of downstream ports 220 for transmitting and/or receiving frames from other nodes, and a Tx/Rx 210 may be coupled to a plurality of upstream ports 250 for transmitting and/or receiving frames from other nodes, respectively. A processor 230 may be coupled to the Tx/Rx 210 to process the frames and/or determine which nodes to send frames to. The processor 230 may comprise one or more multi-core processors and/or memory devices 232, which may function as data stores, buffers, etc. Processor 230 may be implemented as a general processor or may be part of one or more application specific integrated circuits (ASICs) and/or digital signal processors (DSPs). Processor 230 may comprise a content aware module 234, which may provision content forwarding, content caching and content processing in the network as discussed above. Processor 230 may also comprise a conference control module 235, which may provide conference control and management functions, such as conference message exchange described in flowchart 300 and/or flowchart 400. In an alternative embodiment, the content aware module 234 and/or conference control module 235 may be implemented as instructions stored in memory 232, which may be executed by processor 230. The memory module 232 may comprise a cache for temporarily storing content, e.g., a Random Access Memory (RAM). Additionally, the memory module 232 may comprise a long-term storage for storing content relatively longer, e.g., a Read Only Memory (ROM). For instance, the cache and the long-term storage may include dynamic random access memories (DRAMs), solid-state drives (SSDs), hard disks, or combinations thereof.

It is understood that by programming and/or loading executable instructions onto the node 200, at least one of the processor 230, the cache, and the long-term storage are changed, transforming the node 200 in part into a particular machine or apparatus, e.g., a multi-core forwarding architecture, having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an ASIC, because for large production runs the hardware implementation may be less expensive than the software implementation. Often a design may be developed and tested in a software form and later transformed, by well-known design rules, to an equivalent hardware implementation in an ASIC that hardwires the instructions of the software. In the same manner as a machine controlled by a new ASIC is a particular machine or apparatus, likewise a computer that has been programmed and/or loaded with executable instructions may be viewed as a particular machine or apparatus.

Figure 3:
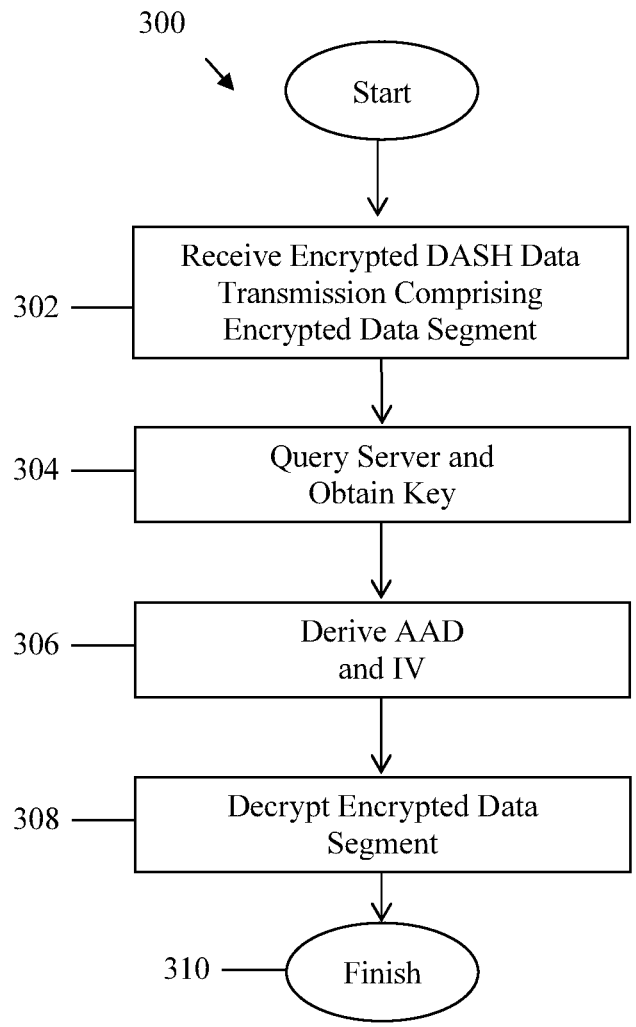
FIG. 3 is a flowchart showing reception of an authenticated encryption session from the point of view of a client.

FIG. 3 is a flowchart 300 showing reception of an authenticated encryption session from the point of view of a client, e.g., streaming client 110 of FIG. 1. At 302, the client may receive, e.g., from a server, e.g., streaming provider 120 of FIG. 1, an encrypted DASH media comprising one or more encrypted segments (E(S)). At 304, the client may query, e.g., by issuing a GET request, and obtain a key (k) from a server, e.g., a dedicated license server, an HTTP server, an HTTPS server, or a DRM server, e.g., streaming provider 120 of FIG. 1. In some embodiments, the key may already be available to the client, e.g., when the key was previously used to decode a previously received encrypted segment. At 306, the client may derive an AAD (a) and an IV (v), e.g., using information contained in the CryptoPeriod described above. In some embodiments, the AAD and/or the IV may be derived by calculation at the client, while in other embodiments the AAD and/or the IV may be calculated remotely and provided to the client. As most DRM systems employ license-based systems to derive keys, license-based key systems are also supported in this disclosure. In such cases, a license may be retrieved, and the key Uniform Resource Identifiers (URIs) may be opaque key identifiers. The license-based key system may resolve these URIs into keys in any way known in the art, and may pass the keys to an encryption system. The latter, having keys provided by the key system and the encryption information (e.g., algorithm specification and IV) provided by the MPD, may decrypt the media segment. The disclosure comprises all such combinations and permutations of deriving the IV and/or ADD. At 308, the client may decrypt the E(S) to obtain a decrypted segment (S), e.g., S=D(E(S), t, k, v, a), wherein 't' is an authentication tag. At 310, the process may finish and the decrypted segment may be utilized, e.g., passed to a media engine and displayed and/or played as a video content.

Figure 4:
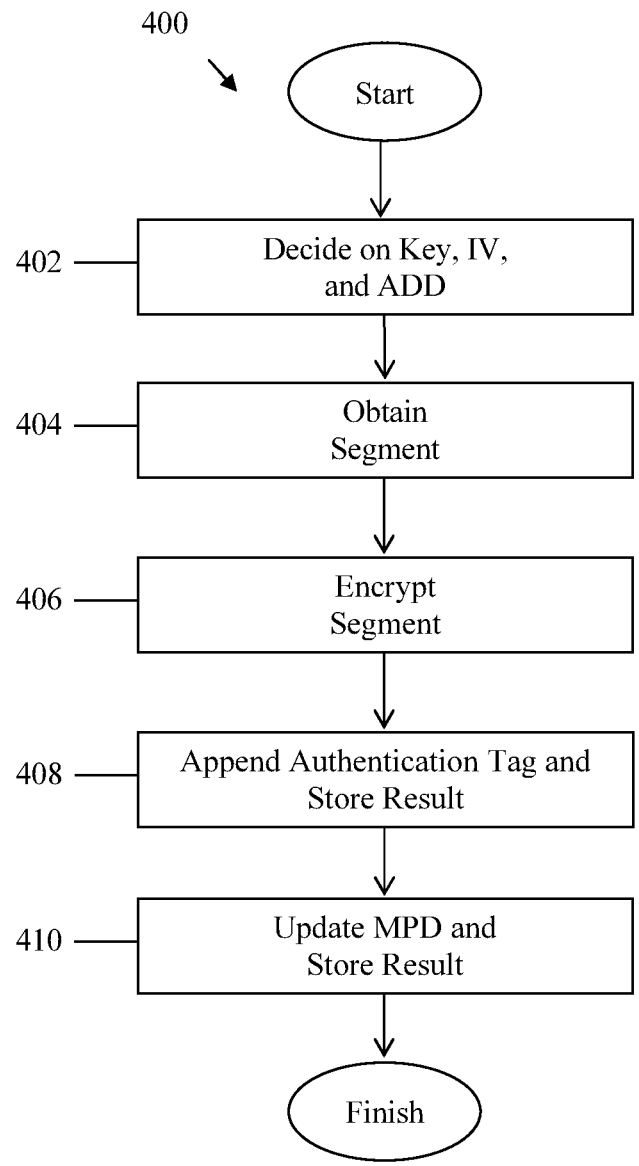
FIG. 4 is a flowchart showing transmission of an authenticated encryption session from the point of view of a server.

FIG. 4 is a flowchart 400 showing transmission of an authenticated encryption session from the point of view of a server, e.g., streaming provider 120 of FIG. 1. At 402, the server may decide on values for the key, the IV, and the ADD, e.g., using techniques known in the art and/or as described supra. At 404, the server may obtain a segment, e.g., from a content server in the system. At 406, the server may encrypt the segment, e.g., using an AES-128 GCM full-segment encryption system. At 408, the server may append an authentication tag to the encrypted segment and may store the result, e.g., at a separate content server. At 410, the server updates the MPD with decrypting information, e.g., how and/or where to get the key, IV, and/or ADD, and may store the result, e.g., at a separate license server. In some embodiments, the server may transmit the encrypted segment with the appended authentication tag to a client, while in other embodiments the server may transmit the encrypted segment to a separate server, e.g., an HTTP/HTTPS server. As will be understood by those of skill in the art, different components and/or a combination of different components may perform steps regarding serving content to the client, e.g., license servers, HTTP/HTTPS servers, dedicated content servers, etc., and the disclosure is not limited to any particular implementation.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. The use of the term "about" means +/−10% of the subsequent number, unless otherwise stated. Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure. The discussion of a reference in the disclosure is not an admission that it is prior art, especially any reference that has a publication date after the priority date of this application. The disclosure of all patents, patent applications, and publications cited in the disclosure are hereby incorporated by reference, to the extent that they provide exemplary, procedural, or other details supplementary to the disclosure.

While several embodiments have been provided in the present disclosure, it may be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

What is claimed is:

1. A server apparatus supporting authenticated encryption in a network, comprising:
 a receiver configured to receive a segment;
 a processor configured to:
  select an encryption key, an initialization vector, and an additional authentication data (AAD);
  obtain an encrypted segment by encrypting the received segment;
  configure the encrypted segment for transfer in a Dynamic Adaptive Streaming over Hypertext Transfer Protocol (HTTP) (DASH) media, wherein the AAD is derived by calculation at the server apparatus;
  assign a segment number to the encrypted segment;
  append an authentication tag to the encrypted segment;
  store the encrypted segment with the appended authentication tag; and
  update a Media Presentation Description (MPD) associated with the encrypted segment with the appended authentication tag, wherein the MPD comprises an @aadBase attribute with an AAD base value, wherein a value of the AAD includes the sum of the segment number and the AAD base value; and
 a transmitter configured to transmit the encrypted segment with the appended authentication tag to a destination.

2. The server apparatus of claim 1, wherein the received segment is encrypted into the encrypted segment using an Advanced Encryption Standard (AES) cipher in Galois/Counter Mode (GCM) mode, wherein the initialization vector length is given by an @ivLength attribute of a SegmentEncryption element, and wherein the authentication tag length is given by an @authTagLength attribute of the SegmentEncryption element.

3. The server apparatus of claim 1, wherein the MPD comprises a @SegmentEncryption@ivEncryptionFlag attribute and a SegmentEncryption@ivLength attribute, wherein the initialization vector is the segment number when the SegmentEncryption@ivEncryptionFlag value is 'false' and the MPD comprises a CryptoPeriod element, wherein the initialization vector is a sum of the segment number and an @ivBase attribute when the SegmentEncryption@ivEncryptionFlag value is 'false' and the MPD comprises a CryptoTimeline element, wherein the initialization vector is an Electronic Codebook (ECB)-encrypted value of a transmitted initialization vector when the SegmentEncryption@ivEncryptionFlag value is 'true' and the MPD does not comprise a CryptoTimeline element or a CryptoPeriod element, wherein the initialization vector is an ECB-encrypted value of the segment number when the SegmentEncryption@ivEncryptionFlag value is 'true' and the MPD comprises a CryptoPeriod element, wherein the initialization vector is an ECB-encrypted value of the sum of the segment number and the @ivBase when the SegmentEncryption@ivEncryptionFlag value is 'true' and the MPD comprises a CryptoTimeline element, and wherein the initialization vector is the first SegmentEncryption@ivLength most significant bit from ECB output when the SegmentEncryption@ivEncryptionFlag value is 'true' and the SegmentEncryption@ivLength is smaller than the output block size of the ECB output.

4. The server apparatus of claim 1, wherein the MPD comprises a CryptoPeriod element, and wherein the AAD is comprised within a CryptoPeriod@aad attribute in the CryptoPeriod element.

5. The server apparatus of claim 1, wherein an authentication tag is appended to a last byte of the encrypted segment.

6. The server apparatus of claim 1, wherein the encrypted segment with the appended authentication tag is one segment in a Period, and wherein a single combination of the encryption key and the initialization vector is used only once during the Period.

7. A computer program product comprising computer executable instructions stored as tangible non-transitory matter on a non-transitory medium that when executed by a processor cause the processor to:
 receive a segment;
 select an encryption key, an initialization vector, and an additional authentication data (AAD), wherein the AAD is derived by calculation at the processor;
 obtain an encrypted segment by encrypting the received segment, wherein the received segment is encrypted using an Advanced Encryption Standard (AES) cipher in Galois/Counter Mode (GCM) mode with an initialization vector with a length given by an @authTagLength attribute of a SegmentEncryption element and an authentication tag with a length given by an @authTagLength attribute of the SegmentEncryption element;

append the authentication tag to the encrypted segment;

configure the encrypted segment with the appended authentication tag for transfer in a Dynamic Adaptive Streaming over Hypertext Transfer Protocol (HTTP) (DASH) media;

assign a segment number to the encrypted segment;

store the encrypted segment with the appended authentication tag;

update a Media Presentation Description (MPD) associated with the encrypted segment with the appended authentication tag, wherein the MPD comprises an @aadBase attribute with an AAD base value, wherein a value of the AAD includes the sum of the segment number and the AAD base value; and transmit the encrypted segment with the appended authentication tag to a destination.

8. The computer program product of claim 7, wherein the MPD comprises a @SegmentEncryption@ivEncryptionFlag attribute and a SegmentEncryption@ivLength attribute, wherein the initialization vector is the segment number when the SegmentEncryption@ivEncryptionFlag value is 'false' and the MPD comprises a CryptoPeriod element, wherein the initialization vector is a sum of the segment number and an @ivBase attribute when the SegmentEncryption@ivEncryptionFlag value is 'false' and the MPD comprises a CryptoTimeline element, wherein the initialization vector is an Electronic Codebook (ECB)-encrypted value of a transmitted initialization vector when the SegmentEncryption@ivEncryptionFlag value is 'true' and the MPD does not comprise a CryptoTimeline element or a CryptoPeriod element, wherein the initialization vector is an ECB-encrypted value of the segment number when the SegmentEncryption@ivEncryptionFlag value is 'true' and the MPD comprises a CryptoPeriod element, wherein the initialization vector is an ECB-encrypted value of the sum of the segment number and the @ivBase when the SegmentEncryption@ivEncryptionFlag value is 'true' and the MPD comprises a CryptoTimeline element, and wherein the initialization vector is the first SegmentEncryption@ivLength most significant bit from ECB output when the SegmentEncryption@ivEncryptionFlag value is 'true' and the SegmentEncryption@ivLength is smaller than the output block size of the ECB output.

9. The computer program product of claim 8, wherein the MPD comprises a CryptoPeriod element, and wherein the AAD is comprised within a CryptoPeriod@aad attribute in the CryptoPeriod element.

10. The computer program product of claim 7, wherein the authentication tag is appended to the last byte of the encrypted segment.

11. The computer program product of claim 7, wherein the encrypted segment with the appended authentication tag is one segment in a Period, and wherein a single combination of the encryption key and the initialization vector is used only once during the Period.

12. The computer program product of claim 7, wherein the AAD for a cryptoperiod (CP(M,D)) is described by the equation $AAD_{CP(M,D)} = SN + aadBase$, wherein SN is the segment number, and wherein aadBase includes the AAD base value.

13. The computer program product of claim 12, wherein the initialization vector is the sum of the segment number and an initialization base value comprised within an @ivBase attribute of a CryptoTimeline element.

14. The computer program product of claim 12, wherein the executable instructions further cause the processor to:

receive a second segment;

encrypt the second received segment using the encryption key, the initialization vector, and the AAD to produce a second encrypted segment; and append a second authentication tag to the second encrypted segment.

15. A method of supporting authenticated encryption at a client node in a network, the method comprising:

receiving a Dynamic Adaptive Streaming over Hypertext Transfer Protocol (HTTP) (DASH) media comprising an encrypted data segment, wherein the media comprises a SegmentEncryption@ivEncryptionFlag attribute, a segment number, and information sufficient to permit the client node to:

query a server for a decryption key;

obtain a decryption key from the server;

derive an initialization vector based on the SegmentEncryption@ivEncryptionFlag attribute;

derive an additional authentication data (AAD);

authenticate an origin of the encrypted data segment; and decrypt the encrypted data segment.

16. The method of claim 15, wherein the media comprises a CryptoPeriod element, and wherein the AAD is comprised within a CryptoPeriod@aad attribute in the CryptoPeriod element.

17. The method of claim 15, wherein a cryptoperiod only consists of a single segment, and wherein no identical combinations of the encryption key and the initialization vector are used within the Period.

18. The method of claim 15, wherein the initialization vector is the segment number when the SegmentEncryption@ivEncryptionFlag is 'false' and the media comprises a CryptoPeriod element, wherein the initialization vector is a sum of the segment number and an @ivBase attribute when the SegmentEncryption@ivEncryptionFlag is 'false' and the media comprises a CryptoTimeline element, wherein the initialization vector is an Electronic Codebook (ECB)-encrypted value of a transmitted initialization vector when the SegmentEncryption@ivEncryptionFlag is 'true' and the media does not comprise a CryptoTimeline element or a CryptoPeriod element, wherein the initialization vector is an ECB-encrypted value of the segment number when the SegmentEncryption@ivEncryptionFlag is 'true' and the media comprises a CryptoPeriod element, wherein the initialization vector is an ECB-encrypted value of the sum of the segment number and the @ivBase when the SegmentEncryption@ivEncryptionFlag is 'true' and the media comprises a CryptoTimeline element, and wherein the media further comprises a SegmentEncryption@ivLength attribute, wherein the initialization vector is a first SegmentEncryption@ivLength most significant bit from ECB output when the SegmentEncryption@ivEncryptionFlag is 'true' and the SegmentEncryption@ivLength is smaller than an output block size of the ECB output.

* * * * *